(12) United States Patent
Hanada et al.

(10) Patent No.: US 7,790,191 B2
(45) Date of Patent: Sep. 7, 2010

(54) COSMETIC COMPOSITION

(75) Inventors: Kazuyuki Hanada, Washimiya-machi (JP); Hiromasa Sato, Kashiwa (JP); Koji Sakuta, Gunma (JP); Akira Yamamoto, Joetsu (JP)

(73) Assignees: Dainichiseika Color & Chemicals Mfg. Co., Ltd., Tokyo (JP); Shin-Etsu Chemical Co., Ltd., Tokyo (JP)

( * ) Notice: Subject to any disclaimer, the term of this patent is extended or adjusted under 35 U.S.C. 154(b) by 1365 days.

(21) Appl. No.: 10/936,483

(22) Filed: Sep. 9, 2004

(65) Prior Publication Data
US 2005/0053571 A1   Mar. 10, 2005

(30) Foreign Application Priority Data
Sep. 10, 2003   (JP) .............................. 2003-318490
Sep. 7, 2004    (JP) .............................. 2004-259518

(51) Int. Cl.
*A61Q 1/00*   (2006.01)
*A61Q 1/06*   (2006.01)
*A61Q 1/10*   (2006.01)
*A61Q 3/02*   (2006.01)
*A61Q 5/00*   (2006.01)
*A61Q 15/00*  (2006.01)

(52) U.S. Cl. .......................... 424/401; 424/59; 424/61; 424/64; 424/65; 424/70.7; 424/70.12

(58) Field of Classification Search .................. None
See application file for complete search history.

(56) References Cited

U.S. PATENT DOCUMENTS 5,643,581 A    7/1997 Mougin et al.
6,166,093 A *  12/2000 Mougin et al. ........... 514/772.1
6,395,265 B1   5/2002 Mougin et al.
2002/0150546 A1 10/2002 Mougin et al.

FOREIGN PATENT DOCUMENTS

| FR | 2 743 297 A | 7/1997 |
| JP | 3-177411 A | 8/1991 |
| JP | 9-12425 A | 1/1997 |
| JP | 10-279650 A | 10/1998 |
| JP | 2002-20221 A | 1/2002 |
| JP | 2003-2945 A | 1/2003 |
| JP | 2005-68228 A | 3/2005 |

* cited by examiner

*Primary Examiner*—Jyothsna A Venkat
(74) *Attorney, Agent, or Firm*—Birch, Stewart, Kolasch & Birch, LLP

(57) ABSTRACT

A cosmetic composition comprising a polysiloxane copolymer comprising a repeating unit (A) having at least one anionic group, a repeating unit (B) having at least one linear or branched alkyl group having 8 to 64 carbon atoms, and a polysiloxane repeating unit (D), said repeating units (A), (B), and (D) being bonded with one another via diisocyanate residue represented by the following formula (1)

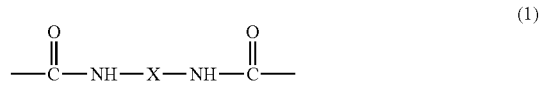

wherein X is a divalent hydrocarbon group selected from the group consisting of aromatic hydrocarbon groups, aliphatic hydrocarbon groups, and alicyclic hydrocarbon groups. Cosmetics comprising the composition maintains their effects for a prolonged period of time.

21 Claims, No Drawings

COSMETIC COMPOSITION

CROSS REFERENCES

This application claims benefits of Japanese Patent application No. 2003-318490 filed on Sep. 10, 2003, and Japanese Patent application No. 2004-259518 the contents of which are hereby incorporated by reference.

FIELD OF THE INVENTION

The present invention relates to a cosmetic composition, specifically to a cosmetic composition comprising a specific film-forming polysiloxane copolymer. The present invention relates also to cosmetics comprising the composition, particularly makeup cosmetics and hair cosmetics, which adhere well to the skin or hair and maintain their effects for a prolonged time.

DESCRIPTION OF THE PRIOR ART

For cosmetics, durability on the skin or hair is important, particularly makeup cosmetics such as foundation, eye shadow, cheek color, eyeliner, mascara, lipsticks, and nail enamel, and hair cosmetics such as shampoo, rinse, and styling hair wax. A film-forming agent is generally used to improve the durability. Examples of the film-forming agents include vinyl type, acrylic type and cellulose type polymers. Improvements in the durability of cosmetics comprising these film-forming agents were tried, for example, by modifying a polymer skeleton, and copolymerizing vinyl or acrylic monomers with different kinds of co-monomers. However, satisfactory durability has not been achieved yet.

In addition to the aforesaid durability, the film-forming agent is desired to have affinity or adherence to the skin or hair, a good film-forming property, water resistance, and oil resistance. Further, flexibility to follow skin movements and usability are also desired for the skin cosmetics. It was difficult to obtain a film-forming agent which satisfies the aforesaid requirements from the vinyl, acrylic or cellulose type polymer. Therefore, a new substance should be sought.

U.S. Pat. No. 5,643,581 discloses a polymer comprising repeating units of a polysiloxane block and a polyurethane block and/or a polyurea block. The polymer shows flexibility, stickiness, water resistance and oil resistance which had not been achieved by the vinyl, acrylic or cellulose type of polymers.

However, the above polymer does not have enough dispersibility or miscibility in hydrocarbon oils or natural oils from animals or plants to give a stable cosmetic. Further, the cosmetic made comprising the polymer does not extend smoothly on the skin or hair, resulting in unsatisfactory usability.

SUMMARY OF THE INVENTION

A purpose of the present invention is to provide a cosmetic composition comprising a film-forming agent without the above problems, and a cosmetic comprising the composition.

The present invention is a cosmetic composition comprising a polysiloxane copolymer comprising a repeating unit (A) having at least one anionic group, a repeating unit (B) having at least one linear or branched alkyl group having 8 to 64 carbon atoms, and a polysiloxane repeating unit (D), said repeating units (A) (B), and (D) being bonded with one another via diisocyanate residue represented by the following formula (1)

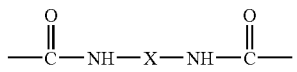

wherein X is a divalent hydrocarbon group selected from the group consisting of aromatic hydrocarbon groups, aliphatic hydrocarbon groups, and alicyclic hydrocarbon groups.

Another aspect of the present invention is a cosmetic comprising the cosmetic composition described above in an amount of from 2 to 95 wt %, based on a total weight of the cosmetic.

Since the polysiloxane copolymer comprises the units comprising relatively long alkyl chains besides the polysiloxane units, the present composition has a good miscibility with commonly used oil agents for cosmetic to give stable and durable cosmetics.

PREFERRED EMBODIMENT OF THE INVENTION

In the diisocyanate residue of the formula (1),

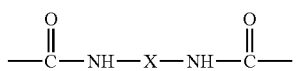

X is a divalent hydrocarbon group selected from the group consisting of aromatic hydrocarbon groups, aliphatic hydrocarbon groups, and alicyclic hydrocarbon groups. Examples of X include hexamethylene, 4,4'-diphenylmethane, p-phenylene, 4,4'-biscyclohexylmethylene, and isophorone groups, among which hexamethylene group is preferred. The diisocyanate residue of the formula (1) may be formed by reacting a diisocyanate compound comprising X with a dial compound. Examples of the diisocyanate compound include hexamethylene diisocyanate, 4,4'-diphenylmethane diisocyanate, 2,4-tolylene diisocyanate, 2,6-tolylene diisocyanate, 1-methylcyclohexylene-2,4-diisocyanate, 1-methylcyclohexylene-2,6-diisocyanate, 4,4'-dicyclohexylmethanediisocyanate, 1,5-naphthylenediisocyanate, 3,3'-dimethyl-4,4'-biphenylene diisocyanate, xylylene diisocyanate, hydrogenated xylylene diisocyanate, isophorone diisocyanate, and 2,2,4-trimethylhexamethylene diisocyanate.

The repeating unit (A) preferably has a group represented by the following formula (2)

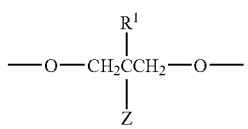

wherein Z is an anionic group. All or a part of the Zs in the polymer may be neutralized by cationic groups. $R^1$ is a methyl or ethyl group. Examples of the anionic group include a carboxylic group, a sulfonic acid group, a phenolic hydroxyl group, or a phosphoric acid group, among which a carboxylic group is preferred. The neutralization may be carried out by a compound having a cationic group such as an inorganic base and an organic base. A degree of the neutralization may range from 10 to 100% equivalent, preferably from 30 to 60% equivalent. The repeating unit (A) may be derived from dimethylolpropanoic acid or dimethylolbutanoic acid.

The repeating unit (B) having at least one linear or branched alkyl group having 8 to 64 carbon atoms preferably has the group represented by the following formula (3).

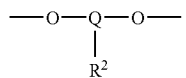
(3)

In the formula (3), $R^2$ is a linear or branched alkyl group having 8 to 64 carbon atoms. The number of carbon atoms and the presence or absence of a branch may preferably be determined mainly depending on an oil agent used in preparing a cosmetic. Typically, $R^2$ is a linear alkyl group having 16 to 38 carbon atoms. In the formula (3), Q is the group of the formula (4), the group of the formula (5) or a mixture thereof.

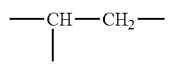
(4)

(5)

The repeating unit (B) may be derived by a diol compound. Examples of the diol include one commercially available under the trade name, AOG-X68, ex Daicel Chemical Industry Ltd., which is represented by the formula, $CH_2(OH)$—CH(OH)—$(CH_2)_nCH_3$, wherein n is an average number of about 20, and has a hydroxyl number of 311 KOH mg/g, and an average molecular weight of 360; and one commercially available under the trade name, AOG-Y08, ex Daicel Chemical Industry Ltd., represented by the formula, $CH_2(OH)$—CH(OH)—$(CH_2)nCH_3$, wherein n is an average number of about 34, and has a hydroxyl number of 204 KOHmg/g and an average molecular weight of 550.

Preferably, the polysiloxane repeating unit (D) is derived from a polysiloxane having a number average molecular weight, reduced to standard polystyrenes, of from 500 to 20,000, preferably 1,000 to 10,000, and 2 hydroxyl groups. The hydroxyl groups may be located at any places in a polysiloxane molecule, but preferably both hydroxyl groups are located all at one terminal of the polysiloxane chain; or each one hydroxyl group at each one terminal. Examples of unit (D) derived from the polysiloxane include one represented by the formula (7) and one represented by the formula (8):

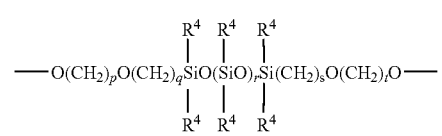
(7)

wherein $R^4$ is an alkyl group having 1 to 7 carbon atoms, p, q, s, and t are integers of from 1 to 5, and r is an integer of from 5 to 60,

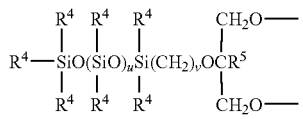
(8)

wherein u is an integer of from 5 to 60, v is an integer of from 1 to 5, $R^4$ has the same meaning as described above and $R^5$ is a hydrogen atom or an alkyl group having 1 to 7 carbon atoms.

The contents of the units (A), (B), and (D) may range from 0.1 to 30 wt %, 1 to 95 wt % and 1 to 95 wt %, based on a total weight of the units (A), (B), and (D), respectively. Preferably, the contents of (A), (B), and (D) may range from 2 to 20 wt %, 2 to 70 wt % and 5 to 95 wt %, based on a total weight of the units (A), (B), and (D), respectively.

The polysiloxane copolymer may comprise the repeating unit (C) which comprises a group represented by the following formula (6) in an amount of from 0.1 to 70 wt %, based on a total weight of the units (A), (B) (C) and (D)

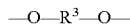
(6)

In the formula (6), $R^3$ a hydrocarbon group having 1 to 20 carbon atoms and may contain at least one selected from the group consisting of O, N, and S atoms. The unit (C) may be derived from a diol compound other than those used for the unit (B). Examples of the diol include ethylene glycol, 1,3-propylene glycol, 1,2-propylene glycol, 1,3-butanediol, 1,4-butanediol, 1,5-pentanediol, 1,6-hexanediol, 3-methyl-1,5-pentandiol, neopentyl glycol, 1,8-octanediol, 1,9-nonanediol, and polycarbonatediol such as one commercially available under the trade name, PLACCEL CD220, ex Daicel Chemical Industry Ltd., among which polycarbonatediol is preferred.

When the polysiloxane copolymer comprises the unit (C), the contents of the units (A), (B), (C), and (D) range from 1 to 20 wt %, 5 to 90 wt %, 1 to 70 wt % and 1 to 80 wt %, based on a total weight of the units (A) to (D), respectively.

The polysiloxane copolymer may be prepared by dissolving, in a polar solvent having no active hydrogen such as tetrahydrofuran, dimethylolpropanoic acid or dimethylolbutanoic acid for the repeating unit (A), a diol compound having a long alkyl chain for the repeating unit (B), the polysiloxane for the unit (D), and optionally the diol for the unit (C) in the amounts described above, adding the diisocyanate and subjecting the mixture thus obtained to a reaction at a temperature of from 50 to 100 degrees C. Completion of the reaction can be confirmed by disappearance of free isocyanate groups in IR spectrometry. The reaction mixture is cooled and homogeneously emulsified with water and an alkaline compound such as NaOH and triethylamine. After evaporating the solvent such as tetrahydrofuran under vacuum, the copolymer is obtained in a form of an aqueous emulsion. When 1,3-butanediol or propylene glycol is used instead of water, the copolymer can be obtained in a form of a nonaqueous emulsion.

A number average molecular weight, reduced to standard polystyrenes, of the obtained polysiloxane copolymer is determined by GPC and preferably in the range of from 2,000 to 100,000. If the number average molecular weight is smaller than the aforesaid lower limit, a film made of the copolymer may be too weak. If the number average molecular weight exceeds the aforesaid upper limit, the copolymer may be difficult to handle.

The present composition can be used for various kinds of cosmetics, particularly those to be applied on skin or hair such as skincare cosmetics, hair cosmetics, antiperspirants, makeup cosmetics, and UV ray protective cosmetics. A content of the composition in the cosmetic may be adjusted according to each cosmetic, but typically ranges from 2 to 95 wt % as an emulsion containing water or a nonaqueous solvent used in neutralization, based on a total weight of the cosmetic.

Preferably, the cosmetic comprises various kinds of components in addition to the present composition, which hereinafter will be referred to as composition (a), such as an oil agent (b). The oil agent (b) may be one or a mixture of oils which are solid, semi-solid, or liquid, at an ambient temperature, among which the one which is liquid at 25 degrees C. is preferred. Examples of the oil agent (b) include natural oils from animals or plants, hydrocarbon oils, a higher fatty acid, higher alcohols, ester oils, silicone oils, and fluorinated oils.

Examples of the oils from animals or plants and semi-synthetic oils include avocado oil, linseed oil, almond oil, Ibota wax, perilla oil, olive oil, cacao butter, kapok wax, kaya oil, carnauba wax, Glycyrrhiza oil, candelilla wax, beef tallow, neat's-foot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shear butter, Chinese tung oil, cinnamon oil, jojoba wax, squalane, olive squalane, squalene, shellac wax, turtle oil, soybean oil, tea seed oil, camellia oil, evening primrose oil, corn oil, lard, rapeseed oil, Japanese tung oil, rice bran oil, germ oil, horse fat, persic oil, palm oil, palm kernel oil, castor oil, hydrogenated castor oil, castor oil fatty acid methyl ester, sunflower oil, grape oil, bayberry wax, jojoba oil, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, hydrogenated lanolin, lanolin alcohol, hard lanolin, lanolin acetate, isopropyl lanolate, POE lanolin alcohol ether, POE lanolin alcohol acetate, lanolin fatty acid polyethylene glycol, POE hydrogenated lanolin alcohol ether, and egg yolk oil. The term "POE" means polyoxyethylene.

Examples or the hydrocarbon oil include linear, branched and volatile hydrocarbons. Examples include α-olefin oligomers, light isoparaffin, light liquid isoparaffin, ozokerite, synthetic squalane, vegetable squalane, ceresin, paraffin, paraffin wax, polyethylene wax, polyethylene-polypropylene wax, liquid paraffin, pristane, polyisobutylene, microcrystalline wax, and Vaseline.

Examples of the higher fatty acid include lauric acid, myristic acid, palmitic acid, stearic acid, behenic acid, undecylenic acid, oleic acid, linoleic acid, linolenic acid, arachidonic acid, eicosapentaenoic acid (EPA) docosahexaenoic acid (DHA), isostearic acid, and 12-hydroxystearic acid.

Examples of the hydrocarbon oil include linear, branched and volatile hydrocarbons. Examples include α-olefin oligomers, ozokeritevegetable squalane, ceresin, paraffin, paraffin wax, polyethylene wax, polyethylene-polypropylene wax, pristane, polyisobutylene, microcrystalline wax, and vaseline.

Examples of the higher fatty acid such as lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxystearic acid.

Examples of the higher alcohol having 11 carbon atoms or more include lauryl alcohol, myristyl alcohol, palmityl alcohol, stearyl alcohol, behenyl alcohol, hexadecyl alcohol, oleyl alcohol, isostearyl alcohol, hexyldodecanol, octyl dodecanol, cetostearyl alcohol, 2-decyltetradecinol, cholesterol, phytosterol, POE cholesterol ether, monostearyl glycerin ether (batyl alcohol), and monooleyl glyceryl ether (cerakyl alcohol).

Examples of the ester oils include diisobutyl adipate, 2-hexyldecyl adipate, di-2-heptylundecyl adipate, N-alkyl glycol monoisostearatet isocetyl isostearate, trimethylolpropane triisostearate, isononyl isononanate, isotridecyl isononanate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprirate, triethyl citrate, 2-ethylhexyl succinate, amyl acetate, ethyl acetate, butyl acetate, isocetyl stearate, butyl stearate, diisopropyl sebacinate, di-2-ethylhexyl sebacinate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, and diisostearyl malate.

Examples of the glyceride oils include acetoglyceryl, glycerol triisooctanoate, glyceryl triisostearate, glyceryl triisopalmitate, glyceryl monostearatet glyceryl di-2-heptylundecanoate, glyceryl trimyristate, and diglyceryl myristyl isostearate.

Examples of the silicone oils include the followings.

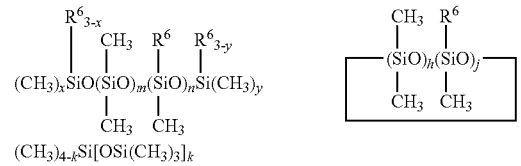

wherein $R^6$ is selected from the group consisting of a hydrogen atom, a hydroxyl group, an alkyl or fluorinated alkyl group having 2 to 20 carbon atoms, an aryl group, an aminoalkyl group, an alkoxy group and a group of the formula, $(CH_3)_3SiO[(CH_3)_2SiO]lSi(CH_3)_2CH_2CH_2$—, m is an integer of from 0 to 1,000, n is an integer of from 0 to 1,000, x is an integer of from 0 to 3, y is an integer of from 0 to 3, h and j are integers of from 0 to 8 with $3 \leq h+j \leq 8$, k is an integer of from 1 to 4, and l is an integer of from 0 to 500.

Examples of $R^6$ include methyl, ethyl, propyl, butyl, hexyl, octyl, decyl, dodecyl, tetradecyl, hexadecyl, octadecyl, trifluoropropy, nonafluorohexyl, heptadecylfluorodecyl, phenyl, aminopropyl, dimetylaminopropyl, aminoethylaminopropyl, stearoxy, butoxy, ethoxy, propoxy, cetyloxy, myristyloxy, stylyl, and α-methylstylyl, among which hexyl, octyl, decyl, dodecyl, dodecyl, tetradecyl, hexadecyl, octadecyl, trifluoropropy, phenyl, aminopropyl, and aminoethylaminopropyl are preferred.

Examples of the silicone oil include organopolysiloxanes having from low to high viscosities, such as dimethylpolysiloxane, methylphenylpolysiloxane, methylhydrogenpolysiloxane and dimethylsiloxane-methylphenylsiloxane copolymer; cyclosiloxanes, such as octamethylcyclotetrasiloxane (D4), decamethylcyclopentasiloxane (D5), dodecamethylcyclohexasiloxane (D6), tetramethyltetrahydrogencyclotetrasiloxane (H4) and tetramethyl-tetraphenylcyclotetrasiloxane; branched siloxanes such as tristrimethylsiloxysilane (M3T), tetrakistrimethylsiloxysilane (M4Q), and tristrimethylsiloxyphenylsilane; higher alcohol-modified silicone such as stearoxysilicone, alkyl-modified silicone, amino-modified silicone and fluoro-modified silicone.

Examples of the fluorinated oil such as perfluoropolyethers, perfluorodecaline, perfluorooctane, fluorinated pitch, fluoroalcohol and a combination thereof.

As the oil agent (b), a solid oil agent having a melting point higher than 50 degrees C. may be used. Examples of the solid oil agent include hydrocarbon oils, e.g., ozokerite, ceresin, paraffin wax, polyethylene wax, polyethylene-polypropylene wax, and microcrystalline wax; higher fatty acids, e.g., palmitic acid, stearic acid, and behenic acid; higher alcohols, e.g., stearyl alcohol, behenyl alcohol, and hexadecyl alcohol; silicone oils, e.g., higher alcohol-modified silicone, and longer alkyl chain-modified silicone; natural fats, oils from animals or plants and semi-synthetic oils such as carnauba wax, liver oil, candelilla wax, bee oil, beeswax, and vegetable tallow wax.

The oil agent (b) content can be varied from 1.0 to 95 wt % according to the form of the cosmetic. Preferably, the content ranges from 1.0 to 50 wt % based on a total weight of the cosmetic. If the content is less than 1.0 wt %, a benefit of the oil agent (b) may not be obtained. If it exceeds 95 wt %, the effect of the present composition (a) may not be enough.

The cosmetics of the present invention may further comprise one or more of a compound (c) having an alcoholic hydroxyl group except the higher alcohol already mentioned above. Examples of the compound having alcoholic hydroxyl group include lower monoalcohols such as ethanol and isopropanol; sugar alcohols such as sorbitol and maltose; sterols such as cholesterol, sitosterol, phytosterol, and lanosterol; polyalcohols such as butylene glycol, propylene glycol, butylene glycol, and pentyl glycol and sugar alcohols. Preferably, a water soluble mono- or poly-alcohol having 2 to 10 carbon atoms is used. The compound (c) may be incorporated in the cosmetic in an amount of from 0.1 to 98 wt % based on a total weight of the cosmetic.

The cosmetic of the present invention may comprise one or more water-soluble polymer and/or water-swelling polymer (d) Examples of the water-soluble or water-swelling polymer include plant polymers such as gum Arabic, tragacanth gum, arabinogalactan, locust bean gum (carob gum), guar gum, karaya gum, carrageenan, pectin, agar, quince seed (i.e., marmelo), starch from rice, corn, potato or wheat, algae colloid, trant gum and locust bean gum; bacteria-derived polymers such as xanthan gum, dextran, succinoglucan, and pullulan; animal-derived polymers such as collagen, casein, albumin, and gelatin; starch-derived polymers such as carboxymethyl starch and methylhydroxypropyl starch; cellulose polymers such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, and cellulose powder; alginic acid-derived polymers such as sodium alginate and propylene glycol alginate; vinyl polymers such as polyvinyl methylether, and carboxyvinyl polymer; polyoxyethylene polymers; polyoxyethylene/polyoxypropylene copolymers; acrylic polymers such as sodium polyacrylate, polyethyl acrylate, and polyacrylamide; synthetic water-soluble polymers such as polyethyleneimine and other kind of cationic polymers; semi-synthetic water-soluble polymers such as silicone-modified pullan; and water-soluble inorganic polymers such as, bentonite, aluminum magnesium silicate, montmorillonite, beidellite, notronite, saponite, hectorite, and silicic anhydride. The examples of the water-soluble polymer further include film forming agents such as polyvinyl alcohol and polyvinyl pyrrolidone. The water-soluble or water-swelling polymer may be incorporated in the cosmetic in an amount of from 0.01 to 25 wt % based on a total weight of the cosmetic.

The present cosmetic may further comprise powder and/or coloring agent (e). Any known powder can be used which is commonly used in cosmetics, regardless of the shape (spherical, rod-like, acicular, tubular, irregular, scaly or spindle forms), particle size (size of fume, fine particles or pigment grade), and particle structure (porous and non-porous), such as, for example, inorganic powder, organic powder, surface activating metal salt powder, colored pigments, nacreous pigments, metallic powder pigments, and natural dyes.

Examples of the inorganic powders include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, biotite, lithia mica, silicic acid, silicic anhydride, aluminum silicate, magnesium silicate, aluminum magnesium silicate, calcium silicate, barium silicate, strontium silicate, metal salts of tungstenic acid, hydroxyapatite, vermiculite, higilite, bentonite, montmorillonite, hectolitre, zeolite, ceramics powder, calcium secondary phosphate, alumina, aluminum hydroxide, boron nitride, and silica.

Examples of the organic powders include polyamide powder, polyester powder, polyethylene powder, polypropylene powder, polystyrene powder, polyurethane, benzoguanamine powder, polymethylbenzoguanamine powder, tetrafluoroethylene powder, polymethylmethacrylate powder, cellulose, silk powder, nylon powder such as Nylon 12 and Nylon 6, spherical silicone elastomer powder having crosslinked dimethylsilicone structure (see Japanese Laid-Open Patent Application No. 3-93834), spherical polymethylsilsesquioxane powder (see Japanese Laid-Open Patent Application No. 3-47848), spherical silicone elastomer powder with its surface coated with polymethylsilsesquioxane (see Japanese Laid-Open Patent Application No. 7-196815) styrene/acrylic acid copolymer, divinylbenzene/styrene copolymer, vinyl resin, urea resin, phenol resin, fluororesin, acrylic resin, melamine resin, epoxy resin, polycarbonate resin, microcrystalline fiber powder, starch powder, and lauroyl lysine.

Examples of the surface activating metal salt powders (metal soaps) include zinc stearate, aluminum stearate, calcium stearate, magnesium stearate, zinc myristate, magnesium myristate, zinc cetyl phosphate, calcium cetyl phosphate, and zinc/sodium cetyl phosphate.

Examples of the colored pigments include inorganic red pigments such as iron oxide, iron hydroxide, and iron titanate, inorganic brown pigments such as γ-iron oxide, inorganic yellow pigments such as iron oxide yellow and loess, inorganic black pigments such as iron oxide black and carbon black, inorganic violet pigments such as manganese violet and cobalt violet, inorganic green pigments such as chromium hydroxide, chromium oxide, cobalt oxide, and cobalt titanate, inorganic blue pigments such as Prussian blue and ultramarine blue, lakes of tar pigments, lakes of natural dyes, and synthetic resin powder complexes thereof.

Examples of the nacreous pigments include titanium oxide-coated mica, bismuth oxychloride, titanium oxide-coated bismuth oxychloride, titanium oxide-coated talc, fish scales, and titanium oxide-coated colored mica and examples of metallic powder pigments include aluminum powder, copper powder and stainless steel powder.

Examples of the tar pigments include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207. Examples of the natural dyes include carminic acid, laccaic acid, carthamin, brazilin, and crocin.

Powders which absorb or scatter UV ray may be used, too, such as titanium oxide fine powder, fine powder of titanium oxide containing iron, zinc oxide fine powder, cerium oxide fine powder and a mixture thereof.

These powders may have been subjected to compounding or surface treatment with common oil agents, conventional silicone oils, fluorine-containing compounds or surfactants prior to use, as far as such treatment does not adversely affect the present cosmetic. Two or more of the aforesaid powders may be used as desired. The powder and/or coloring agent (e) may be incorporated in the cosmetic in an amount of from 0.1 to 99 wt %, particularly from 80 to 90 wt % in a powdery solid cosmetic, based on a total weight of the cosmetic.

The present cosmetic may further comprise one or more or surfactant (f). Any anionic, cationic, non-ionic or amphoteric surfactant can be used in common cosmetics may be used.

Examples of the anionic surfactants include fatty acid soaps, such as sodium stearate and triethanolamine palmitate, alkylether carboxylic acids and salts thereof, salts of amino acids and fatty acids, alkylsulfonic acids, alkenesulfonates, sulfonates of fatty acid esters, sulfonates of fatty acid amides, sulfonates of alkylsulfonate-formalin condensates, alkylsulfates, sulfates of secondary higher alcohols, alkyl/allyl ether sulfates, sulfates of fatty acid esters, sulfates of fatty acid alkylolamides, and sulfates of Turkey Red oil, alkyl phosphates, ether phosphates, alkylallylether phosphates, amide phosphates, and N-acylamino surfactants.

Examples of the cationic surfactants include amine salts such as salts of alkylamine, polyamine and amino alcohol fatty acid derivatives, alkyl quaternary ammonium salts, aromatic quaternary ammonium salts, pyridium salts and imidazolium salts.

Examples of the nonionic surfactants include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkylethers, polyoxypropylene alkylethers, polyoxyethylene alkylphenylether, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanolether, polyoxyethylene phytosterolether, polyoxyethylene cholestanolether, polyoxyethylene cholesterylether, linear or branched polyoxyalkylene-modifed organopolysiloxane, polyglycerin-modified organopolysiloxane, polyoxyalkylene/alkyl co-modified-organopolysiloxane, polyoxyalkylene/alkyl co-modified-organopolysiloxane alknolamide, sugar ethers, and sugar amides.

Examples of the amphoteric surfactants include betaine, aminocarboxylates, and imidazoline derivatives.

Among the aforesaid surfactants, preferred are linear or branched polyoxyalkylene-modified organopolysiloxane, polyoxyalkylene/alkyl co-modified-organopolysiloxane, polyglycerin-modified organopolysiloxane, and polyoxyalkylene/alkyl co-modified-organopolysiloxane. The surfactant may be incorporated in an amount preferably from 0.1 to 20 wt %, more preferably from 0.2 to 10 wt %, based on a total weight of the cosmetic.

The present cosmetic may further comprise one or more of a crosslinked organopolysiloxane (g). Preferably, the crosslinked organopolysiloxane is swelled with a silicone having a viscosity of from 0.65 to 10.0 mm$^2$/sec in a larger amount by weight than the amount of the crosslinked organopolysiloxane itself. This crosslinked organopolysiloxane can be obtained by reacting a SiH bond of organohydrogenpolysiloxane with crosslinking agent having 2 or more of reactive vinylic unsaturated groups in a molecule. Further, the crosslinked organopolysiloxane may have at least one residue selected from the group consisting of polyoxyalkylene residue, alkyl residue, aryl residue, and fluoroalkyl residue. Examples of the crosslinked organopolysiloxane, though not limited to these, include KSG-15, KSG-16, KSG-18, KSG-210, and KSG-710, all of which are in a gel from swelled with a silicone oil and commercially available from Shin-Etsu Chemical Co. The crosslinked organopolysiloxane (g) may be incorporated in the cosmetic in an amount preferably of from 0.1 to 50 wt %, more preferably 1 to 30 wt %.

The present cosmetic may comprise a polysiloxane resin (h) which is in gum form or non-elastomeric solid form at 25 degrees C. and soluble in decamethylcyclopentasiloxane. Examples of the gum form organopolysiloxanes include substituted or unsubstituted organopolysiloxanes having RRSiO units, e.g., dimethylpolysiloxane, methylphenylpolysiloxane, and methylfloroalkylpolysiloxane, or those having a slightly crosslinked structure. In particular, dimethylpolysiloxane gum with a degree of polymerization ranging from 3,000 to 20,000 is desirable.

Examples of the non-elastomeric solid form organopolysiloxanes include those which are commonly called silicone resin compounds, for example, those expressed by the average formula: $R_nSiO_{(4-n)/2}$ and having $RRRSiO_{0.5}$ units (i.e., M units), RRSiO units (i.e., D units), $RSiO_{1.5}$ units (i.e., T units), and $SiO_2$ units (i.e. Q units), wherein the average number of n ranges preferably from 1 to 8. In the formula, R preferably represents a substituted or unsubstituted linear or branched alkyl group having 1 to 30 carbon atoms, or an organic residue having a phenyl group, amino group, polyether group, glycoside derivatives, glyceryl group, or polyglyceryl group, and all of the R groups may be identical or different. Another example is acrylic silicone copolymer resins including acrylic/silicone graft or block copolymers. In particular, silicone copolymer compounds containing at least one moiety selected from the group consisting of pyrrolidone moieties, long-chain alkyl moieties, polyoxyalkylene moieties, fluoroalkyl moieties, and amino moieties are desirable since they improve duration of the cosmetic coverage. Examples of the acrylic silicone copolymer resins are KP545 and KP561, produced by Shin-Etsu Chemical Co., Ltd.

In the cosmetic of the present invention, a variety of components that are commonly used in cosmetics can be blended in addition to the aforementioned components, as far as the purpose of the present invention is not damaged, for example, oil-soluble gelling agents, clay minerals modified with organic compounds, resins, antiperspirants, ultraviolet absorbents, ultraviolet absorbing and scattering agents, moisture retention agents, antiseptics, anti-microbial agents, perfumes, salts, antioxidants, pH regulators, a chelating agents, refreshing agents, an anti-inflammatory agent, skin beautifying components, such as skin whitener, cell activator, rough dry skin improver, blood circulation promoter, skin astringent and anti-seborrheic agent, vitamins, amino acids, nucleic acids, hormones, clathrate compounds, and hair setting agents.

Examples of the oil-soluble gelling agent include metal soaps such as aluminum stearate, magnesium stearate, and zinc myristate; α-amino acid derivatives such as N-lauroyl-L-glutamic acid, α,γ-di-n-butylamine; dextrin fatty acid esters such as dextrin palmitate, dextrin stearate, and dextrin 2-ethylhexane palmitate; sucrose fatty acid esters such as sucrose palmitate and sucrose stearate; fatty acid esters of fructo-oligosaccharide such as inulinstearate, and 2-ethylhexanoic ester of fructo-oligosaccharide; benzylidene derivatives of sorbitol such as monobenzylidene sorbitol and dibenzylidene sorbitol; clay minerals modified with an organic moiety such as dimethylbenzyldodecylammonium montmorillonite clay, dimethyldioctadecylammonium montmorillonite.

Examples of the antiperspirant include aluminum chlorohydrate, aluminum chloride, aluminum sesquichlorohydrate, zirconyl hydroxy chloride, aluminum zirconium hydroxychloride and aluminum zirconium glycine; pH regulators such as lactic acid, citric acid, glycolic acid, succinic acid, tartaric acid, dl-malic acid, potassium carbonate, sodium hydrogen carbonate and ammonium hydrogen carbonate; chlating agents such as alanine, sodium, sodium polyphosphate, sodium metaphosphate, phosphoric acid; refrigerants such as L-menthol and camphor; and anti-inflammatory agents include allantoin, glycyrrhetinic acid, glycyrrhizinic acid, tranexamic acid, and azulene.

Examples of the UV absorbents include UV absorbents of benzoate type, such as p-aminobenzoic acid, ethyl dihydroxypropyl p-aminobenzoate, glyceryl p-aminobenzoate, and octyl p-dimethylaminobenzoate; anthranilic acid type UV absrobents such as methyl anthranilate; UV absorbents of salicylic acid type, such as methyl salicylate, octyl salicylate, and triethanol amine salt or salicylic acid; cinnamic acid type UV absorbents, such as octyl p-methoxycinnamate, diethanol amine salt of p-methoxyhydroxycinnamic acid, and dimethocycinnamic acid/isooctanoic acid gryceride; benzophenone type UV absorbents, such as 2,4-dihydroxybenzophenon, 2,2',4,4'-tetrahydroxybenzophenon, 2-hydroxy-4-methyoxybenzophenon, 2-hydroxy-4-methoxypenzophenon-5-sulfonic acid, 2,2'-dihydroxy-4-methoxypenzophenon, and 2-hydroxy-4-N-octoxybenzophenon; UV absorbents of urocanic acid type, such as ethyl urocanate; UV absorbents of dibenzoylmethane type, such as 4-tert-butyl-4'-methoxydibenzoylmethane, 4-isopropyl dibenzoylmethane; 3-(4-methylbenzylidene) camphor, octyltriazone, e-ethylhexyl-2-cyano-3,3-diphenylacrylate, 2-phenyl-benzoimidasole-5-sulfate, 4-(3,4-dimethoxypnehylmethylene)-2,5-dioxo-1-imidazolidine, and 2-ethylhexylpropionate. The UV absorber may be encapsulated in a polymer powder. The aforesaid powders which absorb or scatter UV ray may be used, for example, titanium oxide fine powder, fine powder of titanium oxide containing iron, zinc oxide fine powder, cerium oxide fine powder and a mixture thereof.

Examples of a moisture retention agent include glycerin, sorbitol, propylene glycol, dipropylene glycol, 1,3-butylene glycol, pentylene glycol, glucose, xylitol, maltitol, polyethylene glycol, hyaluronic acid, chondroitin sulfuric acid, pyrrolidone carboxylate, polyoxyethylene glycoside, and polyoxypropylene methylglycoside.

Examples of the antiseptics or antibacterial agents include alkyl paraoxybenzoates, benzoic acid, sodium benzoate, sorbic acid, potassium sorbate, and phenoxyethanol may be used. For the antibacterial agents, benzoic acid, salicylic acid, carbolic acid, sorbic acid, paraoxybenzoic acid alkyl esters, parachloromethacresol, hexachlorophene, benzalkonium chloride, chlorohexydine chloride, trichlorocarbanilide, triclosan, photosensitizer, and phenoxyethanol.

Examples of salts include inorganic salts, salts of organic acid, amine salts and salts of amino acid. Examples of the inorganic salts include sodium, potassium, magnesium, calcium, aluminum, zirconium, and zinc salt of hydrochloric acid, sulfuric acid, carbonate acid, and nitric acid. Examples of organic acid salts include salts of acetic acid, dehydroacetic acid, citric acid, maleic acid, succinic acid, ascorbic acid, and stearic acid. An example of amine salt is salt of triethanolamine and that of amino acid salt is salt of glutamic acid. Other examples are salts of hyaluronic acid, chondroitin sulfate, aluminum zirconium glycine complex and salts made by acid-base reaction which are allowed to incorporate in cosmetics.

Examples of the antioxidants include tocopherol, butylhydroxyanisole, dibutylhydroxytoluene and phytic acid; examples of the pH regulators include lactic acid, citric acid, glycolic acid, succinic acid, tartaric acid, dl-malic acid, potassium carbonate, sodium hydrogen carbonate and ammonium hydrogen carbonate; examples of the chelating agents include alanine, sodium ethylenediaminetetraacetate, sodium polyphosphate, sodium metaphosphate and phosphoric acid; examples of the refrigerants include L-menthol and camphor; and examples of the anti-inflammatory agents include allantoin, glycyrrhizin and salts thereof, glycyrrhetinic acid and stearyl glycyrrhetinate, tranexamic acid and azulene.

Examples of skin-beautifying components include whitening agents such as placenta extract, arbutin, glutathione and Yukinoshita extract, kojic acid, placenta extract, sulfur, ellagic acid, linoleic acid, tranexamic acid; cell activators, such as royal jelly, photosensitizers, cholesterol derivatives, calf blood extract, α-hydroxy acid and β-hydroxy acid; rough and dry skin improvers; blood circulation improvers, such as nonylic acid vanillyl amide, benzyl nicotinate, β-butoxyethyl nicotinate, capsaicin, zingerone, cantharis tincture, ichtammol, caffeine, tannic acid, α-borneol, tocopheryl nicotinate, inositol hexanicotinate, cyclandelate, cinnarizine, tolazoline, acetyl choline, verapamil, cepharanthin and gamma-oryzanol; skin astringents, such as zinc oxide and tannic acid; and anti-seborrheic agents, such as sulfur and thianthol; and skin colorants such as α-hydroxyacetone.

The present cosmetic may further comprises vitamins in an amount not to adversely affect the invention, e.g. vitamin A such as vitamin A oil, retinol, retinyl acetate and retinyl palmitate; vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and its derivatives, and vitamin $B_{15}$ and its derivatives; vitamin C, such as L-ascorbic acid, L-ascorbate dipalmitate, sodium (L-ascorbic acid)-2-sulfate and dipotassium L-ascorbic acid diphosphate; vitamin D, such as ergocalciferol and cholecarciferol; vitamin E, such as alpha-tocopherol, beta-tocopherol, gamma-tocopherol, dl-alpha-tocopheryl acetate, dl-alpha-tocopheryl nicotinate and dl-alpha-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

Examples of amino acids include glycine, valine, leucine, isoleucine, serine, threonine, phenylaranine, alginine, lysine, aspartic acid, glutamic acid, cystine, cysteine, methionine, and tryptophan; examples or the nucleic acids include deoxyribonucleic acid; and examples of the hormones include estradiol and ethenyl estradiol.

Examples of the polymers for hair setting include amphoteric, anionic, cationic, and nonionic polymers, such as polymers of polyvinyl pyrrolidone type such as polyvinyl pyrrolidone, vinyl pyrrolidone/vinyl acetate copolymers; acidic polymers of vinyl acetate ether type such as methyl vinyl ether/maleic acid anhydride alkyl half ester copolymer; polymers of acidic poly vinyl acetate type such as vinyl acetate/ crotonic acid copolymer; acidic acrylic polymers such as (meth) acrylic acid/alkyl (meth) acrylate copolymer, (meth) acrylic acid/alkyl (meth)acrylate/alkyl acrylic amide copolymer, and amphoteric acrylic polymer such as N-methacryloylethyl-N,N-dimethylammonium alpha-N-methylcarboxybetaine/alkylmetahcrylate copolymer, hydroxypropyl (metha)acrylate/butylaminoethyl methacrylate/octyl amide of acrylic acid copolymer. Use is also made of naturally occurring polymers such as cellulose or derivatives thereof, keratin, collagen and derivatives thereof.

The cosmetic may be skincare products, such as face lotion, milky lotion, cream, cleansing, pack, liquid oil, massage materials, washing agent, deodorant, hand cream, and lip cream; hairdressing products such as shampoo, rinse, treatment, setting agent, and hair wax; antiperspirant; makeup products, such as makeup base, face powder, liquid foundation, oil foundation, cheek color, eye shadow, mascara, eyeliner, eyebrow lipstick, and nail enamel; and ultraviolet protection cosmetics, such as sunscreen milky lotion or sunscreen cream.

The present cosmetic may be in various forms such as liquid, milky lotion, cream, solid, paste, gel, powder, pellet, lamella, mousse, stick, spray and pencil form.

EXAMPLES

The present invention will be further explained by referring to the examples, though not be limited to these examples. In the examples, "%" means "% by weight" unless otherwise specified.

Example 1

A reactor provided with a stirrer, a condenser, a thermometer, a nitrogen gas inlet, and an inlet for feeding raw materials was purged by nitrogen gas. Then, 28.9 g of dimethylolbutanoic acid for deriving the unit (A), 40 g of AOG-X68 for unit (B), ex Daicel Chemical Industry Ltd., having a hydroxyl number of 311 KOH mg/g, 160 g of polysiloxane for the unit (D) of the following formula having a hydroxyl number of 59 KOH mg/g, and 196 g of tetrahydrofuran were placed in the reactor to make a homogeneously dissolved solution.

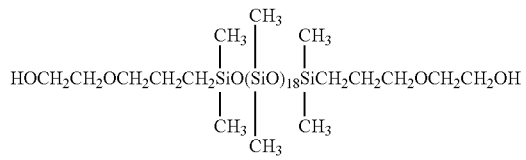

To the solution, 65.5 g of hexamethylene diisocyanate was added and the mixture obtained was subjected to a reaction at 80 degrees C. until it was confirmed that an IR peak of free isocyanate group at 2,270 cm$^{-1}$ disappeared. Then, the reaction mixture was cooled to 50 degrees C., to which deionized water in an amount corresponding to 40 wt % of non-volatile components in the reaction mixture, and 3.9 g of NaOH corresponding to a half the equivalent amount of the carboxyl group in dimethylolbutanoic acid were added to make a homogeneous emulsion. Then, the emulsion was subjected to a vacuum distillation to remove tetrahydrofuran, and there remained a composition in emulsion form. By drying the composition, a copolymer having an acid number of 0.66 KOH mg/g and a number average molecular weight of 12,100 was obtained.

Example 2

Procedures in Example 1 were repeated except that 43.1 g of dimethylolbutanoic acid, 40 g of AOG-X68, 40 g of PLACCEL CD220 for deriving the unit (C) having a hydroxyl number of 56 KOH mg/g, and 120 g of the polysiloxane were dissolved in 216 g of tetrahydrofuran. To the solution, 81.5 g of hexamethylene diisocyanate was added and the mixture obtained was subjected to a reaction at 80 degrees C. until it was confirmed that an IR peak of free isocyanate group at 2,270 cm$^{-1}$ disappeared. Then, the reaction mixture was cooled to 50 degrees C. To the cooled reaction mixture, deionized water in an amount corresponding to 40 wt % of non-volatile components in the reaction mixture, and 3.5 g of NOH corresponding to 30% of the equivalent amount of the carboxyl group in dimethylolbutanoic acid were added to make a homogeneous emulsion.

Then, the emulsion was subjected to a vacuum distillation to remove tetrahydrofuran, and there remained a composition in emulsion form. By drying the composition, a copolymer having an acid number of 0.90 KOH mg/g and a number average molecular weight of 10,100 was obtained.

Example 3

Procedures in Example 1 were repeated except that 24.5 g of dimethylolpropanoic acid, 80 g of AOG-Y08 having a hydroxyl number of 204 KOH mg/g, 120 g of the following polysiloxane having a hydroxyl number of 35 KOH mg/g were dissolved in 191 g of tetrahydrofuran.

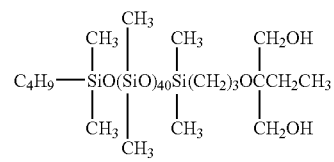

To the solution, 61.5 g of hexamethylene diisocyanate was added and the mixture obtained was subjected to a reaction at 80 degrees C. until it was confirmed that an IR peak of free isocyanate group at 2,270 cm$^{-1}$ disappeared. Then, the reaction mixture was cooled to 50 degrees C., to which deionized water in an amount corresponding to 40 wt % of non-volatile components in the reaction mixture, and 6.5 g of triethylamine corresponding to 35% of the equivalent amount of the carboxyl group in dimethylolpropanoic acid were added to make a homogeneous emulsion.

Then, the emulsion was subjected to a vacuum distillation to remove tetrahydrofuran, and there remained a composition in emulsion form. By drying the composition, a copolymer having an acid number of 0.64 KOH mg/g and a number average molecular weight of 13,200 was obtained.

Example 4

Procedures in Example 2 were repeated except that 21.5 g of dimethylolpropanoic acid, 60 g of AOG-Y08, 40 g of PLACCEL CD220, 100 g of the polysiloxane as used in Example 3 was dissolved in 184 g of tetrahydrofuran. To the solution, 53.8 g of hexamethylene diisocyanate was added and the mixture obtained was subjected to a reaction at 80 degrees C. until it was confirmed that an IR peak of free isocyanate group at 2,270 cm$^{-1}$ disappeared. Then, the reaction mixture was cooled to 50 degrees C., to which deionized water in an amount corresponding to 40 wt % of non-volatile components in the reaction mixture, and 6.5 g of triethylamine corresponding to 40% of the equivalent amount of the carboxyl group in dimethylolpropanoic acid were added to make a homogeneous emulsion.

Then, the emulsion was subjected to a vacuum distillation to remove tetrahydrofuran, and there remained a composition in emulsion form. By drying the composition, a copolymer having an acid number of 0.58 KOH mg/g and a number average molecular Weight of 12,500 was obtained.

Chemical structures of AOG-X68, AOG-Y08, PLACCEL CD220 are as follows:

AOG-X68; 1,2-hydroxylalkane, ex Daicel Chemical Industry Ltd, $CH_2(OH)$—$CH(OH)$—$(CH_2)_nCH_3$, with n being about 20 on average, and an average molecular weight of 360.

AOG-Y08: 1,2-hydroxylalkane, ex Daicel Chemical Industry Ltd, $CH_2(OH)$—$CH(OH)$—$(CH_2)_nCH_3$, with n being about 34 on average, and an average molecular weight of 550.

PLACCEL CD220; polycarbonatediol, ex Daicel Chemical Industry Ltd, $HO(C_6H_{12}OC(=O)O)_nC_6H_{12}OH$, with n being about 13 and an average molecular weight of 2,000.

Example 5

O/W Type Liquid Foundation

| Components | wt % |
| --- | --- |
| 1. Stearic acid | 1.0 |
| 2. Behenyl alcohol | 0.4 |
| 3. Glyceryl monostearate | 0.3 |
| 4. Liquid paraffin | 10.0 |
| 5. Trioctanoin | 5.0 |
| 6. Stearyl-modified acrylate silicone[1] | 3.0 |
| 7. Sorbitan sesquioleate | 0.5 |
| 8. Polysolvate 80 | 1.0 |
| 9. Acrylic acid/alkyl copolymer (30% aqueous solution) | 2.0 |
| 10. 1,3-butylene glycol | 3.0 |
| 11. triethanolamine | 1.0 |
| 12. The composition obtained in Example 1 | 8.0 |
| 13. Pigment | 10.0 |
| 14. Purified water | 62.0 |

[1]KP-561P (ex Shin-Etsu Chemical Co., Ltd.)

(Preparation Method)

Step 1 Components 1-7 and 8 were heated to melt.

Step 2 Components 9-12 and a part of component 14 were mixed and heated.

Step 3 Component 13 was added to the rest of component 14 and dispersed.

Step 4 The resulting mixture from Step 3 was added to that from Step 1 to make an emulsion.

Step 5 The resulting mixture from Step 3 was mixed with that from Step 4.

The O/W type liquid foundation thus obtained extended smoothly on the skin and gave non-tacky touch. It adhered well to the skin and lasted long.

Example 6

Lipstick

| Components | wt % |
| --- | --- |
| 1. Dextrin fatty acid ester | 9.0 |
| 2. Trioctanoin | 18.0 |
| 3. Phenylpolysiloxane[1] | 4.0 |
| 4. Organic-modified Bentonite | 1.0 |
| 5. Polyether modified silicone[2] | 1.5 |
| 5. Decamethylpentasiloxane | 40.5 |
| 6. 1,3-butylene glycol | 3.0 |
| 7. The composition obtained in Example 4 | 6.0 |
| 8. Pigment | 8.0 |
| 9. Purified water | 9.0 |

[1]KF-54, ex Shin-Etsu Chemical Co., Ltd.
[2]KF-6028, ex Shin-Etsu Chemical Co., Ltd.

(Preparation Method)

Step 1: Components 1-6 and Component 10 were mixed while heating.

Step 2: Components 7-9 were mixed and heated.

Step 3: To the resulting mixture from Step 1, the mixture from Step 2 was added and emulsified.

The W/O type lipstick thus obtained extended smoothly, adhered well to the lips and lasted long.

Example 7

O/W Mascara

| Components | wt % |
| --- | --- |
| 1. Stearic acid | 1.0 |
| 2. Cetyl alcohol | 0.5 |
| 3. Monoglyceryl stearate | 0.5 |
| 4. Beeswax | 7.0 |
| 5. Carnauba wax | 2.0 |
| 6. Trioctanoin | 3.0 |
| 7. Sorbitan sesquioleate | 0.7 |
| 8. Polysolvate 80 | 1.5 |
| 9. 1,3-butylene glycol | 5.0 |
| 10. Acrylic acid/alkyl copolymer (30% aqueous solution) | 2.5 |
| 11. The composition obtained in Example 1 | 25.0 |
| 12. Triethanolamine | 0.7 |
| 13. Pigment | 10.0 |
| 14. Purified water | 40.6 |

(Preparation Method)

Step 1 Components 1-8 were heated to melt.

Step 2 To the resulting mixture from Step 1, Component 13 was added and dispersed.

Step 3 Component 9-12, and 14 were mixed while heating.

Step 4 The resulting mixture from Step 3 was added to that from Step 2 to make an emulsion.

The o/w type mascara thus obtained lifted lushes well and stayed long.

Example 8

Eyeliner

| Components | wt % |
| --- | --- |
| 1. Stearic acid | 1.0 |
| 2. The composition obtained in Example 3 | 50.0 |
| 3. Acrylic acid/alkyl copolymer (30% aqueous solution) | 2.5 |
| 4. Triethanolamine | 0.7 |
| 5. Polyoxyethylene alkyl phosphate | 0.2 |
| 6. Pigment | 15.0 |
| 7. 1,3-butylene glycol | 6.0 |
| 8. Purified water | 24.6 |

(Preparation Method)
Step 1 Components 1-4 and a portion of Component 8 were mixed.
Step 2 Components 5-7 was added to the rest of Component 8 and dispersed.
Step 3 The resulting mixture from Step 2 was added to that from Step 1.
The eyeliner thus obtained adhered well to the eyelids and stayed long.

Example 9

Hair Set Lotion

| Components | wt % |
| --- | --- |
| 1. The composition obtained in Example 1 | 8.0 |
| 2. Carboxylvinyl polymer (1% aqueous solution) | 20.0 |
| 3. Triethanolamine | 0.2 |
| 4. 1,3-butylene glycol | 6.0 |
| 5. Purified water | 65.8 |

(Preparation Method)
Components 1 to 5 were mixed.
The hair set lotion thus obtained had a good and long lasting setting property.

Example 10

Nail Enamel

| Components | wt % |
| --- | --- |
| 1. The composition obtained in Example 2 | 80.0 |
| 2. Ethanol | 10.0 |
| 3. Dye | 3.0 |
| 4. Purified water | 7.0 |

(Preparation Method)
Components 1 to 4 were mixed.
The aqueous nail enamel thus obtained was safe and gave a long-lasting glossy finish.

Comparative Example

Procedures in Example 1 were repeated except that 28.9 g of dimethylolbutanoic acid and 370.8 g of the siloxane were used and that AOG-X68 was not used. Using the copolymer thus instead of the composition of Example 1, A O/W liquid foundation was prepared in the same manner as in Example 5. The foundation thus obtained did not spread as lightly as the foundation of Example 5; showed poor usability and the coverage was less stable.

INDUSTRIAL APPLICABILITY

The present composition has a good compatibility with various kinds of oil agents to give cosmetics which has good usability, extend smoothly on the skin or hair and maintain their effects for a prolonged period of time.

The invention claimed is:

1. A cosmetic composition comprising a polysiloxane copolymer comprising a repeating unit (A) having a group represented by the following formula (2)

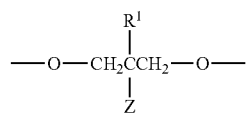
(2)

wherein Z is an anionic group which may be neutralized by a cationic group and $R^1$ is a methyl or ethyl group, a repeating unit (B) represented by the following formula (3)

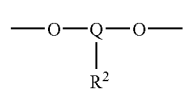
(3)

wherein $R^2$ is a linear or branched alkyl group having 8 to 64 carbon atoms, Q is a group of the following formula (4), a group of the following formula (5), or a mixture thereof

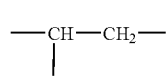
(4)

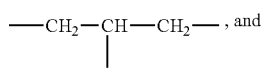
(5)

a polysiloxane repeating unit (D) derived from a polysiloxane having two hydroxyl groups and a number average molecular weight of from 500 to 20,000, said repeating units (A), (B), and (D) being bonded with one another via diisocyanate residue represented by the following formula (1)

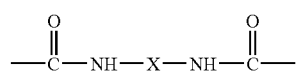
(1)

wherein X is a divalent hydrocarbon group selected from the group consisting of hexamethylene, diphenylmethane-4,4'-diyl, p-phenylene, dicyclohexylmethane-4,4'-diyl, 2,4-tolylene, 3,3-dimethyl-5-methyl-5-ylomethylcyclohexyl, 2,6-tolylene, 1-methylcyclohexylene, 1,5-naphthylene, 3,3'-dimethyl-4,4'-biphenylene, xylylene, hydrogenated xylylene, and 2,2,4-trimethylhexamethylene groups.

2. The cosmetic composition according to claim 1, wherein the anionic group is a carboxylic group.

3. The cosmetic composition according to claim 1, wherein contents of units (A), (B), and (D) range from 0.1 to 30 wt %, 1 to 95 wt % and 1 to 95 wt %, based on a total weight of the units (A), (B), and (D), respectively.

4. The cosmetic composition according to claim 1, wherein the polysiloxane copolymer further comprises a repeating unit (C) represented by the following formula (6) in an amount of from 0.1 to 70 wt %, based on a total weight of the units (A), (B), (C) and (D)

(6)

wherein $R^3$ is a hydrocarbon group having 1 to 20 carbon atoms and may contain at least one selected from the group consisting of O, N, and S atoms, said repeating units (A), (B), (C) and (D) being bonded with one another via the diisocyanate residue represented by formula (1).

5. The cosmetic composition according to claim 4, wherein contents of the units (A), (B), (C), and (D) range from 1 to 20 wt %, 5 to 90 wt %, 1 to 70 wt % and 1 to 80 wt %, based on a total weight of the units (A), (B), (C), and (D), respectively.

6. The cosmetic composition according to claim 1, wherein the polysiloxane copolymer has a number average molecular weight, reduced to standard polystyrenes, of from 2,000 to 100,000.

7. The cosmetic composition according to claim 1, wherein the cosmetic composition is in a form of an emulsion.

8. A cosmetic comprising the cosmetic composition according to claim 1 in an amount of from 2 to 95 wt %, based on a total weight of the cosmetic.

9. The cosmetic according to claim 8, wherein the cosmetic further comprises an oil agent (b).

10. The cosmetic according to claim 9, wherein the oil agent (b) comprises at least one oil which is liquid at 25 degrees C.

11. The cosmetic according to claim 9, wherein the oil agent (b) comprises a silicone oil which is volatile at 25 degrees C.

12. The cosmetic according to claim 9, wherein the oil agent (b) comprises a solid oil which has a melting point of as least 50 degrees C.

13. The cosmetic according to claim 8, wherein the cosmetic further comprises a compound (c) having an alcoholic hydroxyl group and having less than 11 carbon atoms.

14. The cosmetic according to claim 13, wherein the compound (c) having an alcoholic hydroxyl group is water-soluble mono- or poly-hydric alcohol comprising 2 to 10 carbon atoms.

15. The cosmetic according to claim 8, wherein the cosmetic further comprises a water-soluble polymer and/or water-swelling polymer (d).

16. The cosmetic according to claim 8, wherein the cosmetic further comprises powder and/or a coloring agent (e).

17. The cosmetic according to claim 8, wherein the cosmetic further comprises a surfactant (f).

18. The cosmetic according to claim 8, wherein the cosmetic further comprises a crosslinked organopolysiloxane (g).

19. The cosmetic according to claim 18, wherein the crosslinked organopolysiloxane (g) is in a form swelled with a silicone having a viscosity of from 0.65 to 10.0 $mm^2$/sec at 25 degrees C. in a larger amount by weight than an amount by weight of the crosslinked organopolysiloxane itself.

20. The cosmetic according to claim 8, wherein the cosmetic further comprises a polysiloxane resin (h) which is in a gummy form or non-elastomeric solid form at 25 degrees C. and soluble in decamethylcyclopentasiloxane.

21. The cosmetic according to claim 8, wherein the cosmetic is a skincare cosmetic, a hair cosmetic, an antiperspirant, a makeup cosmetic, or an ultraviolet protection cosmetic.

* * * * *